United States Patent
Goo

(10) Patent No.: US 10,213,259 B2
(45) Date of Patent: Feb. 26, 2019

(54) MEDICAL LASER TREATMENT DEVICE AND METHOD FOR OPERATING SAME

(71) Applicant: Lutronic Corporation, Gyeonggi-do (KR)

(72) Inventor: Bon Cheol Goo, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 498 days.

(21) Appl. No.: 14/360,533

(22) PCT Filed: Nov. 26, 2012

(86) PCT No.: PCT/KR2012/010076
§ 371 (c)(1),
(2) Date: May 23, 2014

(87) PCT Pub. No.: WO2013/077712
PCT Pub. Date: May 30, 2013

(65) Prior Publication Data
US 2014/0324033 A1    Oct. 30, 2014

(30) Foreign Application Priority Data
Nov. 24, 2011    (KR) ........................ 10-2011-0123561

(51) Int. Cl.
*A61B 18/20*    (2006.01)
*A61B 18/00*    (2006.01)

(52) U.S. Cl.
CPC .......... *A61B 18/201* (2013.01); *A61B 18/203* (2013.01); *A61B 2018/0091* (2013.01);
(Continued)

(58) Field of Classification Search
CPC .......... A61B 18/201; A61B 2018/2015; A61B 2018/202; A61B 18/203;
(Continued)

(56) References Cited

U.S. PATENT DOCUMENTS 4,985,029 A     1/1991  Hoshino
5,968,033 A  *  10/1999  Fuller ................. A61B 18/203
                                                                606/16
(Continued)

FOREIGN PATENT DOCUMENTS

| JP | 2000-135223 A | 5/2000 |
| WO | 0121256 A1 | 3/2001 |
| WO | WO 2008027438 * | 3/2008 |

OTHER PUBLICATIONS

International Search Report for International Application No. PCT/KR2012/010076 dated Feb. 28, 2013.

*Primary Examiner* — Ahmed Farah

(57) ABSTRACT

The present invention relates to a medical laser treatment device and a method for operating same, which aim to treat a curved area on the skin of a patient. The medical laser treatment device, according to the present invention, comprises: a main body portion having a laser oscillation portion for oscillating the laser; a hand piece, which is connected to the main body, for irradiating the laser onto the skin of the patient; and a laser tip, which is positioned between the skin of the patient and the hand piece and comes into contact with the skin of the patient so as to guide the laser, wherein the laser tip applies pressure to one side of a blood vessel on the inside of an irradiation area.

8 Claims, 5 Drawing Sheets

(52) U.S. Cl.
CPC ............... *A61B 2018/00184* (2013.01); *A61B 2018/00458* (2013.01)

(58) Field of Classification Search
CPC ........... A61B 2018/00452; A61B 2018/00458; A61B 2018/00315; A61B 2018/00398; A61B 2018/00404; A61B 2018/0041; A61B 2018/0091
USPC ................ 606/9, 10, 13, 17–18; 607/88–91; 128/898
See application file for complete search history.

(56) References Cited

U.S. PATENT DOCUMENTS

| | | | | |
|---|---|---|---|---|
| 6,074,383 | A | 6/2000 | Grippi et al. | |
| 6,264,649 | B1 * | 7/2001 | Whitcroft | A61B 18/203 604/113 |
| 6,306,130 | B1 * | 10/2001 | Anderson | A61B 18/203 606/10 |
| 6,605,080 | B1 * | 8/2003 | Altshuler | A61B 18/203 606/13 |
| 6,758,845 | B1 * | 7/2004 | Weckwerth | A61B 18/203 128/898 |
| 7,153,298 | B1 * | 12/2006 | Cohen | A61B 18/203 606/11 |
| 7,431,719 | B2 * | 10/2008 | Altshuler | A61B 18/203 606/9 |
| 2007/0083190 | A1 | 4/2007 | Domankevitz | |

* cited by examiner

MEDICAL LASER TREATMENT DEVICE AND METHOD FOR OPERATING SAME

RELATED APPLICATIONS

This application is a 35 U.S.C. § 371 National Stage filing of International Application No. PCT/KR2012/010076 filed on Nov. 26, 2012, which claims the benefit of Korean Patent Application No. 10-2011-0123561 filed on Nov. 24, 2011. The entire contents of each of the foregoing applications are explicitly incorporated herein by reference.

TECHNICAL FIELD

The present invention relates to a medical laser treatment device and a method of operating the same, and more particularly to a medical laser treatment device that radiates a medical laser to the skin of a patient with an affected part.

BACKGROUND ART

Recently, treatment technologies using a laser have been popularized. Treatment devices using a laser have been used for ophthalmic, dental, and surgical operations and the dermatology.

In general, the treatment devices using a laser which are used for diseases such as skin diseases or vascular diseases achieve their treatment object by radiating a laser with predetermined wavelength and intensity to a skin.

A laser treatment device of the related art has been disclosed in Korean Patent Application Publication No. 2007-0108132, titled "INTERCHANGEABLE TIPS FOR MEDICAL LASER TREATMENTS AND METHODS FOR USING SAME". The prior art document, as shown in FIGS. 8a and 8b, includes a handpiece for radiating a laser to an affected part and a tip at one end of the handpiece.

However, the tip disclosed in the document has a problem in that it is difficult to treat an affect part with many curves of a patient such as the part around the nose or the groove of the upper lip, because it has a structure that equally comes in contact with one flat surface.

DISCLOSURE

Technical Problem

The present invention has been made in an effort to provide a medical laser treatment device having an improved tip structure to treat an affected part of a skin, and a method of operating the medical laser treatment device.

Technical Solution

A medical treatment device according to an aspect of the present invention includes; a body including laser generator that generates a laser; a handpiece connected to the body and radiating a laser to the skin of a patient; and a laser tip disposed between the skin of a patient and the handpiece and guiding a laser in contact with the skin of a patient, in which the laser tip has a cross-section with a predetermined angle in the transverse direction with respect to the irradiation area and presses a side of a blood vessel inside the irradiation area.

The laser tip may have a cross-section with a predetermined angle in the transverse direction with respect to the irradiation area.

The laser tip may be disposed in the longitudinal direction of the blood vessel inside the irradiation area and may press one side of longitudinal direction of the blood vessel so that the blood vessel in the irradiation area expands.

The laser tip may have a support connected to the handpiece and guides extending from the support, and the guide may have: a body having a first contact portion pressing a longitudinal one side of the blood vessel in contact with the skin of a patient and a second contact portion extending upward to the support from the first contact portion; and a guide hole formed in the body and guiding the medical laser to the blood vessel expanded by the first contact portion.

The laser tip may have an inclined cross-section.

One side of the laser tip may have a curved cross-section.

The laser tip may be positioned on a curved area on the skin of a patient.

A method of operating a medical laser treatment device, which includes a body having a laser generator and a handpiece connected to the body, according to another aspect of the present invention includes: (a) bringing the handpiece in contact with the skin of a patient by means of an operator; (b) pressing one side of longitudinal direction of a blood vessel under the skin of a patient with the handpiece being in contact with the skin of a patient; and (c) radiating a laser to the skin of a patient by operating the laser generator in the body.

The medical laser treatment device may further include a laser tip connected to a side of the handpiece and guides a laser to the skin of a patient.

The laser tip may be brought in contact with the skin of a patient, may have a cross-section having a predetermined angle inclined transversely with respect to the skin of a patient, and may press a side of the blood vessel.

The step (b) may press one side of longitudinal direction of the blood vessel so that the blood vessel under the skin of a patient expands.

The laser tip may have an inclined cross-section.

One side of the laser tip may have a curved cross-section.

The step (a) may position the laser tip to a curved area on the skin of a patient.

The details of other embodiments are included in the following detailed description and the accompanying drawings.

Advantageous Effects

According to the medical laser treatment device and a method operating the device of the present invention, it is possible to improve the treatment effect by using a laser tip that can press a side of a skin of a patient where fine blood vessels are gathered.

Further, it is possible to improve the treatment effect by using a laser tip that can fit to curved portions of a patient such as the nose.

MODE FOR INVENTION

Hereinafter, a medical laser treatment device according to an embodiment of the present invention and a method of operating the medical laser treatment device are described in detail with reference to the accompanying drawings.

Before the description, although it is described below that the medical laser treatment device according to the present invention is used for dermatology, it should be understood that the present invention can be used in various fields such as scalp other than dermatology.

Figure 1:
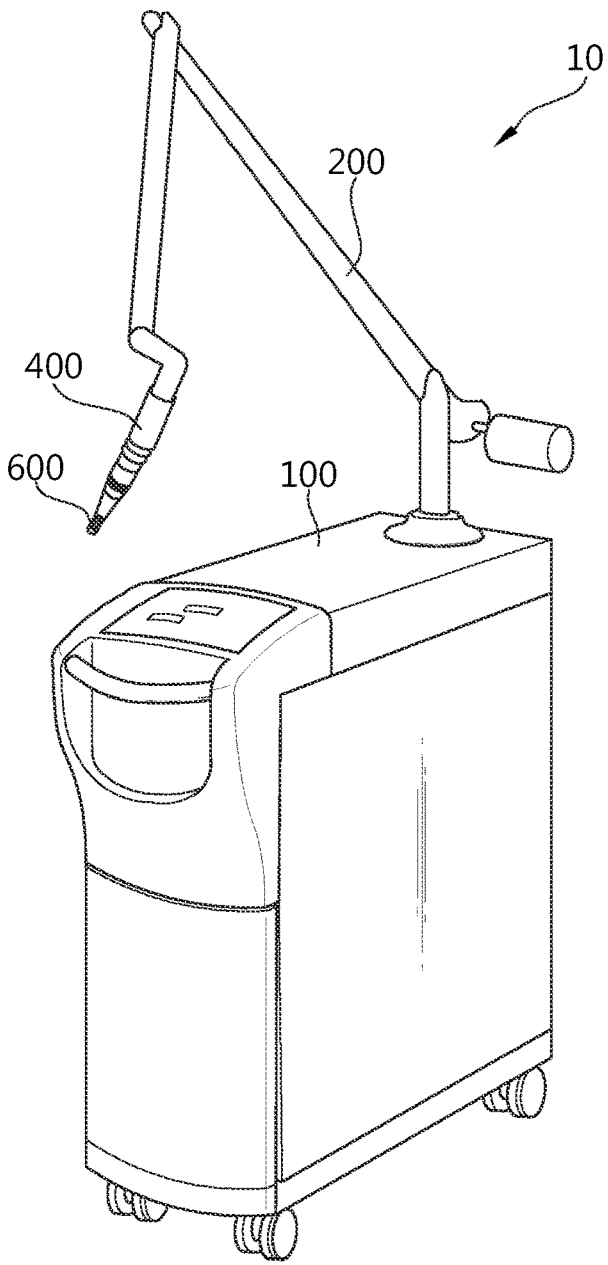
FIG. 1 is a perspective view of a medical laser treatment device according to the present invention.

FIG. 1 is a perspective view of a medical laser treatment device according to the present invention.

As shown in FIG. 1, a medical laser treatment device 10 according to the present invention includes a body 100, a handpiece 400, and a laser tip 600. The medical laser treatment device 10 according to the present invention is preferably used for parts with many bends such as the nose and the groove of the upper lip in the skin 1 of a human body. Obviously, the medical laser treatment device 10 according to the present invention may be used for skins 1 other than the nose and the groove of the upper lip.

The body 100 receives a laser generator (not shown) that generates a medical laser to be radiated to an affected part of the skin 1. The body 100 receives an input unit, a driving unit, and a control unit, which are not shown though.

A connecting unit 200 connects the body 100 and the handpiece 400 with each other. The connecting unit 200 may be formed like a link so that the position of the handpiece 400 can be adjusted by an operator holding the handpiece 400.

The handpiece 400 is connected to the body 100, held by an operator, and moved to the skin 1 of a patient to which a medical laser needs to be radiated. The handpiece 400 radiates the medical laser from the laser generator in the body 100 to the skin 1 of the patient.

The handpiece 400 receives the medical laser from the laser generator through a bending arm (not shown) and is held by an operator so that the medical laser is radiated to an operation object such as the skin 1. The handpiece 400 may include a wavelength converter (not shown) that changes a medical laser with a first wavelength from the laser generator into a medical laser with a second wavelength and outputs it and a filter (not shown) that transmits only the light with the second wavelength of the medical lasers from the wavelength converter.

The laser generator that provides a medical laser to the handpiece 400 is a medical Q-switching Nd:YAG laser that generates a wavelength in a band of 1064 nm and the second wavelength is 2700-3000 nm (preferably, 2936 nm). The laser generator, which is a medical Q-switching Nd:YAG laser, has been well known before filling of this application, so the detailed description is not provided.

Figure 2:
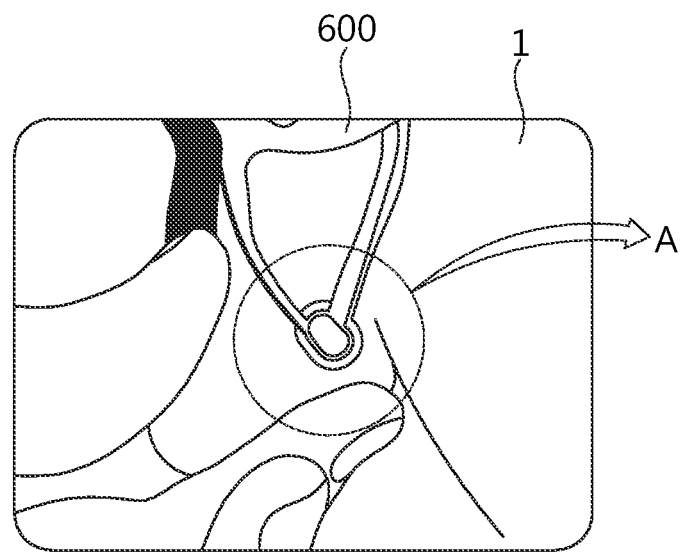
FIG. 2 is a view showing an example of using the laser tip shown in FIG. 1 on the skin of a patient.
Figure 3:
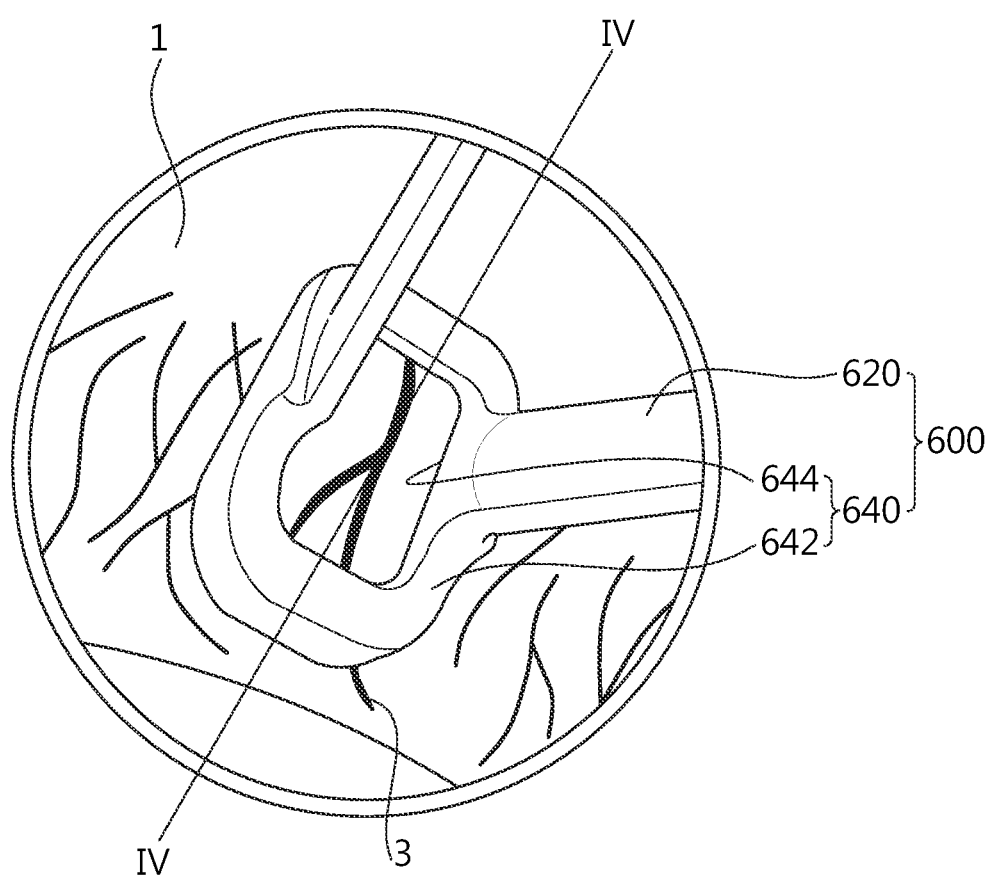
FIG. 3 is an exploded perspective view of the part A shown in FIG. 2.
Figure 4:
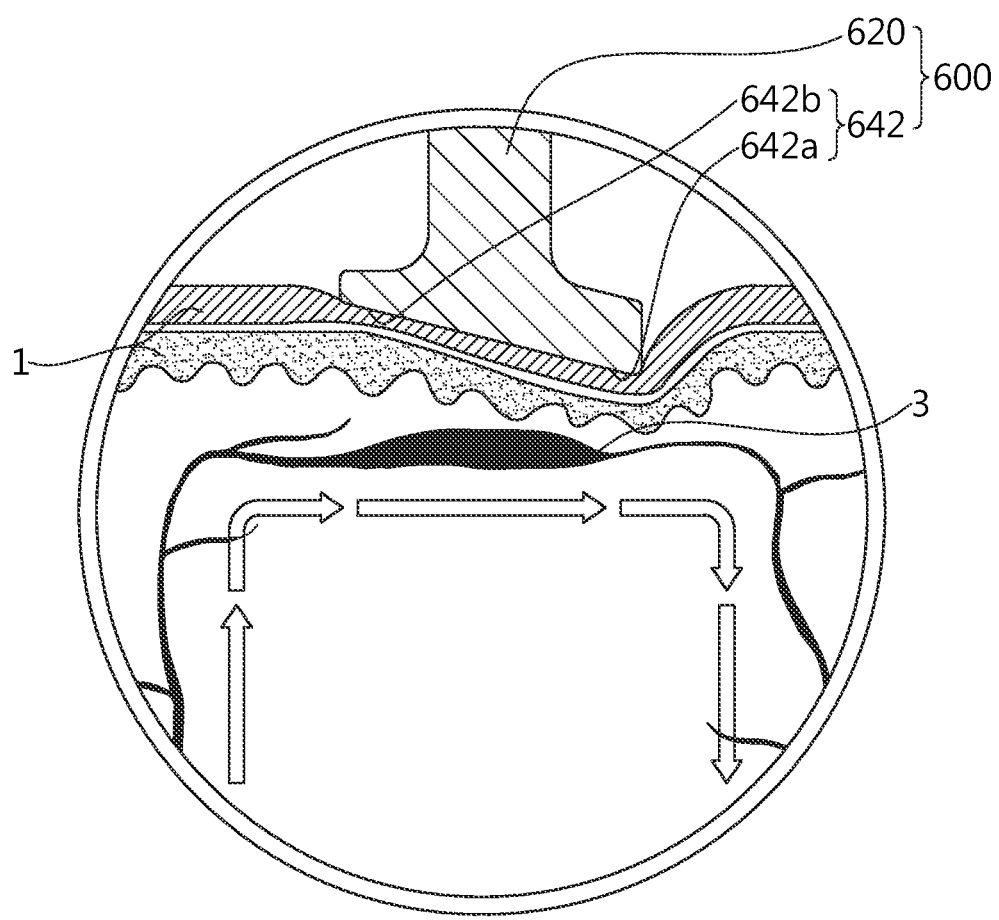
FIG. 4 is a cross-sectional view taken along line IV-IV shown in FIG. 3.

FIG. 2 is a view showing an example of using the laser tip shown in FIG. 1 on the skin of a patient, FIG. 3 is an exploded perspective view of the part A shown in FIG. 2, and FIG. 4 is a cross-sectional view taken along line IV-IV shown in FIG. 3.

As shown in FIGS. 2 to 4, a laser tip 600 is disposed between the skin 1 of the patient and the handpiece 400 and guides the medical laser radiated from the handpiece 400 to the skin 1 of the patient, in contact with the skin 1 of the patient. The laser tip 600 presses a longitudinal part of the internal blood vessel 3 under the skin 1 of the patient so that the blood vessel 3 expands.

The laser tip 600 of the present invention includes a support 620 and a guide 640. The laser tip 600 functions as a sighting device in contact with the skin 1 of the patient which needs to be treated so that the medical laser from the handpiece 400 is guided exactly to the desired position. The laser tip 600 is detachably connected to one end of the handpiece 400 for sterilization. Various sizes of laser tips 600 are detachably mounted on one end of the handpiece 400. The laser tip 600 is preferably brought in contact with the nose of a patient which has many bends, that is, the skin 1 with vessels having a high blood current speed, as shown in FIG. 2.

The support 620 guides the portion between the guide 640 and the handpiece 400. The support 620 is detachably mounted on the handpiece 400. The support 620 of the present invention is provided in a pair connected with both sides of the guide 640.

The guide 640 has a guide body 642 and a guide hole 644. The guide body 642 is connected to the pair of supports 620 and brought in contact with the skin 1 of the patient. The guide body 642 has the shape of a hollow closed loop. That is, as shown in FIG. 3, the guide body 642 has the structure of a hollow rectangular closed loop and the empty are inside the guide body 642 is the guide hole 644. The guide hole 644 defines an area through which a medical laser is irradiated from the handpiece 400.

The guide body 642 has a first contact portion 642a and a second contact portion 642b. The guide body 642 has an inclined cross-section, as shown in FIG. 4. Obviously, the guide body 642 may have a shape with one side curved.

The first contact portion 642a presses the skin 1 of the patient, with the laser tip 600 in contact with the skin 1 of the patient. The first contact portion 642a presses a longitudinal portion of the blood vessel 3 so that the blood vessel 3 expands. As the first contact portion 642a presses a longitudinal portion of the blood vessel 3, the blood vessel 3 expands. The red corpuscles are kept in the blood vessel 3 expanded by the first contact portion 642a, such that the amount of chromophore in the blood vessel 3 can be temporarily increased. The chromophore means a substance in a human body which has a feature of absorbing and changing light with specific wavelengths into heat and discharging it or self-breaking. As in the present invention, the corpuscles in the blood vessel 3 are used as chromophore in treatment of an affected part of the blood vessel 3 under the skin 1. That is, in the corpuscles, when a laser with a predetermined wavelength is radiated and relatively large energy is absorbed, it is changed into heat and the discharged energy damages the structure of the blood vessel wall around, such that the blood vessel with a diseased structure is removed.

As in the present invention, the reason that the first contact portion 642a presses a longitudinal portion of the blood vessel 3 so that the blood vessel 3 expands is because when there is a large amount of chromophore, treatment is possible even with a small amount of energy, but the flow of blood is substantially fast in the bending parts of a human body such as the face, the portions around the nose, and the groove of the upper lip, such that the time for conversion and diffusion of heat energy is insufficient and thus the treatment efficiency decreases. As in the present invention, since the first contact portion 642a can expand the blood vessel 3 by pressing it, it is possible to treat the skin 1 where the flow of blood is fast.

The second contact portion 642b is formed at a higher position than the first contact portion 642a on the skin 1 of the patient. That is, the second contact portion 642b extends upward to the support 620 from the first contact portion 642a. Substantially, the second contact portion 642b does not press the blood vessel 3 even though the first contact portion 642a presses it due to the height difference between the first contact portion 642a and the second contact portion 642b.

Figure 5:
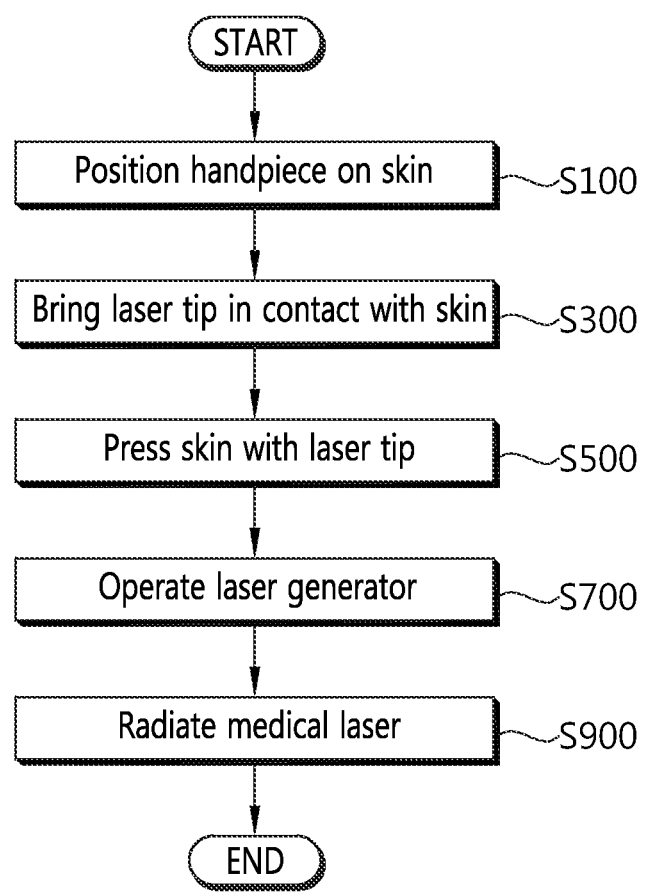
FIG. 5 is a flowchart illustrating an operation using the medical laser treatment device according to the present invention.

Finally, FIG. 5 is a flowchart illustrating an operation using the medical laser treatment device according to the present invention.

A method of operating the medical laser treatment device 10 according to the present invention which has the configuration described above is described below with reference to FIG. 5.

First, an operator holds and moves the handpiece 400 over the skin 1 of the patient with an affected part (S100). That is, as the operator holds and moves the handpiece 400 to the skin 1 of the patient, the handpiece 400 is moved by the connecting unit 200 that connects the body 100 with the handpiece 400. The operator brings the laser tip 600 in contact with the skin of the patient after positioning the handpiece 400 over the skin 1 of the patient with an affected part (S300).

When the operator presses the skin 1 of the patient, one side of the skin 1 of the patient is pressed in accordance with the shape of the laser tip 600 having the inclined cross-section (S500). The laser tip 600 expands the blood vessel 3 to be treated by pressing a side of the skin 1 of the patient, that is, a side of the passage of the blood vessel 3.

Further, the operator operates the laser generator in the body 100 to radiate a medical laser to the laser tip 600 through the handpiece 400 (S700). The blood vessel 3 expanded by the laser tip 600 is treated by the radiated medical laser.

It is possible to improve the treatment effect by using a laser tip that can press a side of a skin of a patient where fine blood vessels are gathered.

Further, it is possible to improve the treatment effect by using a laser tip that can fit to curved portions of a patient such as the nose.

Although embodiments of the present invention were described above with reference to the accompanying drawings, those skilled in the art would understand that the present invention may be implemented in various ways without changing the necessary features or the spirit of the prevent invention. Therefore, the embodiments described above are only examples and should not be construed as being limitative in all respects. The scope of the present invention is defined by not the specification, but the following claims, and all of changes and modifications obtained from the meaning and range of claims and equivalent concepts should be construed as being included in the scope of the present invention.

The invention claimed is:

1. A method of operating a medical laser treatment device, which includes a body having a laser generator and a handpiece connected to the body, the method comprising:
   (a) contacting skin of a patient with the handpiece;
   (b) pressing a portion of a blood vessel by pressing a first area of the skin with the handpiece so as to expand a portion of the blood vessel, the pressed portion of the blood vessel being located under the first area of the skin, the expanded portion of the blood vessel being located upstream of the pressed portion of the blood vessel; and
   (c) irridiating a laser into a second area of the skin under which the expanded portion of the blood vessel is located by operating the laser generator in the body,
   wherein the medical laser treatment device further comprises a laser tip detachably coupled to the handpiece, the laser tip including a guide body that has a specific shape, the specific shape defining the second area of the skin into which the laser irradiates.

2. The method of claim 1, wherein the laser tip is connected to a side of the handpiece and guides the laser to the skin of the patient.

3. The method of claim 2, wherein the laser tip contacts with the skin of the patient, and has a cross-section having a predetermined angle inclined transversely with respect to the skin of the patient.

4. The method of claim 1, wherein the laser tip has an inclined cross-section.

5. The method of claim 4, wherein in the step (a) the laser tip is positioned in a curved area on the skin of the patient.

6. The method of claim 1, wherein the laser tip further includes a pair of supports that are coupled to respective side portions of the guide body and detachably coupled to an end portion of the handpiece.

7. The method of claim 1, wherein the specific shape of the guide body is a closed loop shape.

8. The method of claim 1, wherein the guide body includes a first contact portion and a second contact portion, the first contact portion contacting the first area of the skin when the first area of the skin is pressed with the handpiece, and
   wherein the first contact portion has a thickness greater than that of the second contact portion.

* * * * *